(12) United States Patent
Koyakutty et al.

(10) Patent No.: US 9,402,918 B2
(45) Date of Patent: Aug. 2, 2016

(54) CORE-SHELL PARTICLE FORMULATION FOR DELIVERING MULTIPLE THERAPEUTIC AGENTS

(71) Applicants: Manzoor Koyakutty, Kochi (IN); Parwathy Chandran, Kochi (IN); Archana P. R., Kochi (IN); Shantikumar Nair, Kochi (IN)

(72) Inventors: Manzoor Koyakutty, Kochi (IN); Parwathy Chandran, Kochi (IN); Archana P. R., Kochi (IN); Shantikumar Nair, Kochi (IN)

(73) Assignee: Amrita Vishwa Vidyapeetham, Kochi (IN)

( * ) Notice: Subject to any disclaimer, the term of this patent is extended or adjusted under 35 U.S.C. 154(b) by 0 days.

(21) Appl. No.: 14/465,521

(22) Filed: Aug. 21, 2014

(65) Prior Publication Data
US 2014/0363514 A1 Dec. 11, 2014

Related U.S. Application Data

(63) Continuation of application No. PCT/IN2013/000008, filed on Feb. 19, 2013.

(30) Foreign Application Priority Data

Feb. 21, 2012 (IN) .............................. 644/CHE/2012

(51) Int. Cl.
| | |
|---|---|
| A61K 47/48 | (2006.01) |
| A61K 9/16 | (2006.01) |
| A61K 31/436 | (2006.01) |
| A61K 31/44 | (2006.01) |
| A61K 31/337 | (2006.01) |
| A61K 31/506 | (2006.01) |
| A61K 45/06 | (2006.01) |
| A61K 9/51 | (2006.01) |
| A61K 31/437 | (2006.01) |

(52) U.S. Cl.
CPC ........... *A61K 47/48876* (2013.01); *A61K 9/167* (2013.01); *A61K 9/5138* (2013.01); *A61K 9/5153* (2013.01); *A61K 9/5161* (2013.01); *A61K 9/5169* (2013.01); *A61K 31/337* (2013.01); *A61K 31/437* (2013.01); *A61K 31/44* (2013.01); *A61K 31/506* (2013.01); *A61K 45/06* (2013.01); *A61K 47/489* (2013.01); *A61K 47/48892* (2013.01); *A61K 47/48907* (2013.01); *A61K 47/48923* (2013.01); *A61K 9/5192* (2013.01); *A61K 47/48384* (2013.01)

(58) Field of Classification Search
None
See application file for complete search history.

(56) References Cited

U.S. PATENT DOCUMENTS

2007/0053845 A1* 3/2007 Sengupta ............. A61K 9/1271
424/46

FOREIGN PATENT DOCUMENTS

WO WO2004/089291 * 10/2004

* cited by examiner

*Primary Examiner* — Bethany Barham
*Assistant Examiner* — Barbara Frazier
(74) *Attorney, Agent, or Firm* — Convergence Intellectual Property Law P.C.; Jonathan Garfinkel

(57) ABSTRACT

A core-shell particle formulation for delivering multiple therapeutic agents is disclosed. More particularly, core-shell particle formulation configured to independently release therapeutic agents from the core and the shell. Moreover, the core-shell particle bearing therapeutic agents enables treatment against the diseases such as cancer, inflammatory and auto-immune diseases.

11 Claims, 7 Drawing Sheets

CORE-SHELL PARTICLE FORMULATION FOR DELIVERING MULTIPLE THERAPEUTIC AGENTS

CROSS-REFERENCES TO RELATED APPLICATIONS

This application is a continuation of PCT international application PCT/IN2013/00008 filed on 19 Feb. 2013, which claims priority to Indian patent application No. 644/CHE/2012, filed on 21 Feb. 2012, the full disclosure of which is incorporated herein by reference.

FIELD OF THE INVENTION

This invention relates generally to a core-shell particle formulation for delivering multiple therapeutic agents. More particularly, core-shell particle formulation configured to independently release therapeutic agents from the core and the shell. Moreover, the core-shell particle bearing therapeutic agents enables treatment against the diseases such as cancer, inflammatory and auto-immune diseases.

BACKGROUND

Effective treatments for patients with cancer represented a major challenge in the medical field. The current regimen of surgical resection, external beam radiation therapy, and systemic chemotherapy has been partially successful in some kinds of malignancies. In some malignancies, such as brain malignancies, this regimen produces a median survival of less than one year. Though effective in some kinds of cancers, the use of systemic chemotherapy reached only minor success in the treatment of cancers of the colon-rectum, esophagus, liver, pancreas, and kidney, and skin. A major problem with systemic chemotherapy for the treatment of these types of cancers is that the systemic drug release required for control over tumor growth cell.

Efforts to improve delivery of chemotherapeutic agents to the tumor site have resulted in advances in organ-directed chemotherapy, for example, by continuous systemic infusion. However, continuous infusions of anticancer drugs generally have not shown a clear benefit over pulse or short-term infusions. Some of the prior arts are as follows, US20070053845 discloses a drug delivery system of two different therapeutic agents by means of a core nanoparticle with one therapeutic agent and an outer layer coating of the said core as a shell nanoparticle with second therapeutic agent. The coating of the therapeutic agent as the outer shell delivers the drugs in the faster or even in uncontrollable rate, when compared to the drug delivery from the core.

WO2007069272 discloses a composition for cancer therapy comprises nanoparticles of at least one anticancer drug and at least one polymer. WO2007119601 discloses a pharmaceutical composition with the nanoparticles of platelet-derived growth factor (PDGF) receptor tyrosine kinase inhibitor.

Most of the FDA approved nanoformulations and other drug delivery systems reported till date are single agent delivery vehicles which pose structural constraints to encapsulate and release multiple payloads in optimal concentrations at the tumor site. Encapsulation of more than one drug in the same nano-carrier may elicit undesirable drug-drug interaction which might alter the pharmacology of both the drugs, resulting in inefficacy of the drugs.

However, there remains a need for a drug delivery system for delivering combination therapies so that each agent provides the desired maximal effect. Moreover, the drug delivery system must deliver multiple therapeutic agents and independently release therapeutic agents toward targeted diseased sites.

SUMMARY OF THE INVENTION

A core-shell particle formulation for delivering multiple therapeutic agents is disclosed. In one aspect the formulation comprises one or more polymers forming a core and one or more proteins forming a shell encapsulating the core to form a particle formulation. In various aspects, the core and the shell each comprise one or more therapeutic agents and the particle formulation is configured to independently release therapeutic agents from the core and the shell. In one aspect, the therapeutic agents are configured to be delivered by either passive or active targeting.

In one aspect, the core is of average size ≤500 nm and the shell is of average thickness ≤200 nm respectively. In various aspects, the core and shell are loaded with one or more small molecule kinase inhibitors and chemotherapeutic drugs. In one aspect, the shell comprises one or both of hydrophilic and hydrophobic therapeutic agents. The therapeutic agents are configured to be delivered from the shell and core either sequentially or simultaneously.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 6A shows the flow cytometric apoptosis data of the untreated KG1a cells, (FIG. 6B) KG1a cells treated with 10 nM nano everolimus, (FIG. 6C) 1 μM nano sorafenib and (FIG. 6D) 10 nM everolimus+1 μM sorafenib particle formulation using annexin V FITC and PI staining FIGS. 6E and 6F represent the confocal microscopic images showing both apoptotic and late apoptotic cell fractions.

DETAILED DESCRIPTION

Figure 1A:
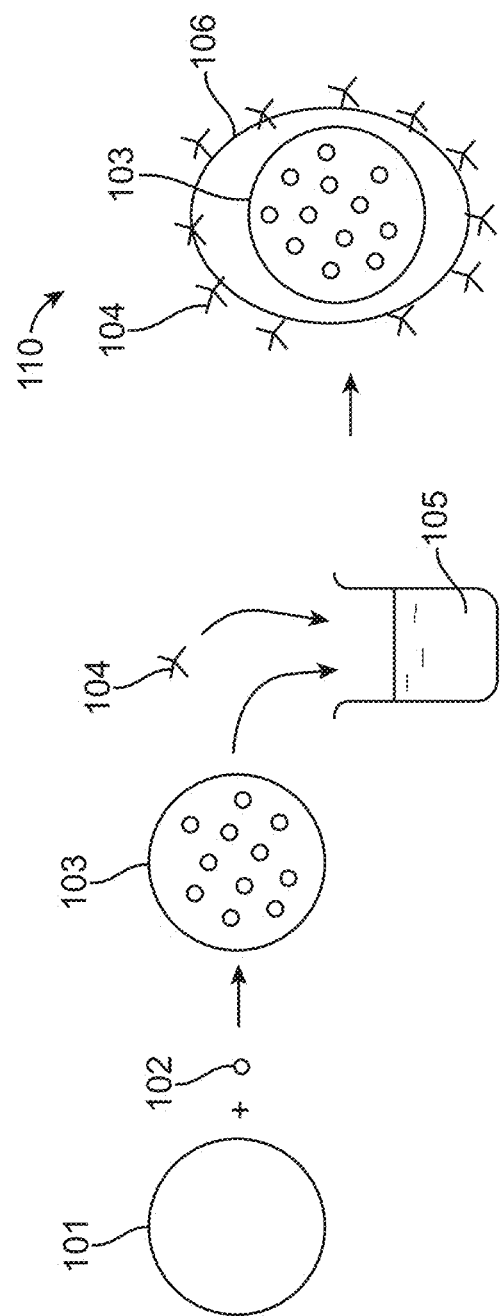
FIG. 1A illustrates a nanoparticle core-shell formulation according to one embodiment.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The term "nanomedicine" as used herein may refer to nanoparticles of protein, polymer or their combinations, measuring size about 1-1000 nm capable of delivering multiple anti-cancer agents such as chemotherapeutic drugs, small molecule inhibitors etc., in different combinations of at least one small molecule kinase inhibitor and one chemotherapeutic drug or suitable combination of two small molecule inhibitors/chemotherapeutic drugs together. In one embodiment the nanoparticles have a size around 1-500 nm. In another embodiment the nanoparticles have a size around 1-200 nm in size.

"Polymer-core/polymer-shell and polymer-core/protein-shell nanomedicine" may refer to nanomedicine constructs comprising a nano-core formed by one type of polymer loaded with one type of chemotherapeutic drug and an outer nano-shell formed by another type of polymer loaded with another drug. Alternatively, the shell can be formed by a protein.

Nanomedicine may be formed by encapsulating at least one therapeutic agent within a biocompatible and biodegradable polymeric nano-core and encapsulating at least one therapeutic agent within a biocompatible polymer/protein nano-shell and connecting the disease targeting ligands to the surface of the nano-shell. Nanomedicine may have a size of 1-1000 nm. In one embodiment the nanomedicine has a size of 1-300 nm. The nanomedicine may be produced in the form of lyophilized powders or liquid dispersions.

Therapeutics may be small molecule kinase inhibitors, chemotherapeutic drugs, prodrugs, etc. that have a therapeutic effect against diseases including cancer, inflammatory and auto-immune diseases and the like.

Small-molecule kinase inhibitors may be synthetic or natural compounds, typically of a molecular size of less than 1,000 Daltons that selectively inhibit particular kinases, typically through ATP-competitive interactions with the catalytic pocket or through allosteric interactions with other regions of the kinase.

The term "combinatorial therapy" as used herein refers to simultaneous use of two or more therapeutics to treat a single disease.

The term "targeting ligand" as used herein refers to active biomolecules that can specifically identify and target an antigen or receptor on the surface of cell-membrane of cancer cells. Targeting ligands may include antibodies, peptides, aptamers, vitamins like folic acid, sugar molecules like mannose, carbohydrates etc.

The term "pharmacokinetics" as used herein refers to the fate of substances administered externally to the body, including their rate and extent of liberation, absorption, distribution, metabolism and excretion.

The proposed invention relating to core-shell particle formulation for delivering multiple therapeutic agents is described in the following sections referring to the sequentially numbered figures. The above-mentioned objectives are achieved through the core-shell particle bearing therapeutic agents specifically targeted to the preferred site of action and configured to controllably release therapeutic agents.

Figure 1B:
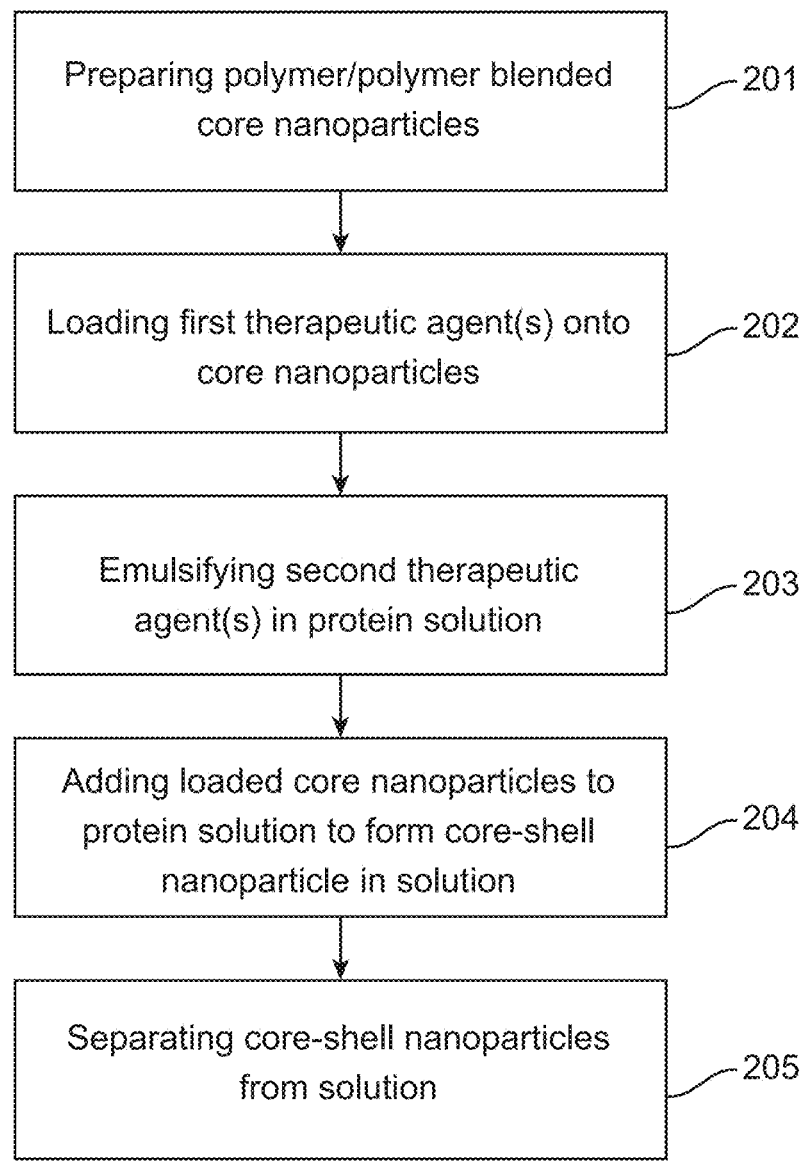
FIG. 1B is a schematic of the method of preparing a core-shell formulation of the invention.

In one embodiment, core-shell particle formulations for delivering multiple therapeutic agents and methods for their preparation are disclosed, as shown in FIGS. 1A and 1B, respectively. As shown in FIG. 1A, in one embodiment, the formulations of the invention comprise one or more polymers to form a core 101 and one or more proteins forming a shell 106. In various embodiments, the core 101 and the shell 106 each comprise one or more therapeutic agents. In one embodiment of the invention illustrated in FIG. 1B, the formulation is obtained using the steps shown in the figure. In step 201, nanoparticles comprising one or more polymers are prepared. In step 202, the core nanoparticles 101 are coated with a therapeutic agent 102 to obtain core nanoparticle 103 loaded with the agent. In step 203, a therapeutic agent 104 is blended with protein 105 for forming the protein shell. The drug-loaded core nanoparticles 103 are added to the blended protein 105 in step 204. In step 204, the therapeutic agent 104 is incorporated into the protein 105 and forms a shell around the core 103. Finally, in step 205, the fully formed core-shell nanoparticles 110 are separated from solution for therapeutic use.

The particle formulation is configured to independently release therapeutic agents 104 from the core 101 and the shell 102. The shell 102 encapsulates the core 101 to form a particle formulation 103. The particle formulations are used for combinational therapy against the diseases such as cancer, inflammatory and auto-immune diseases.

In various embodiments, the polymers for the core 101 are natural or synthetic biocompatible polymer at least one from the group, but not limited to poly glycolic acid (PGA), poly (lactic-co-glycolic acid) (PLGA), glycolide/trimethylene carbonate copolymers (PGA/TMC), poly-lactides (PLA), poly-L lactide (PLLA), poly-DL-lactide (PDLLA), L-lactide/DL-lactide copolymers, lactide/tetramethyl-glycolide copolymers, poly-caprolactone (PCL), poly-valerolacton (PVL), poly-hydroxy butyrate (PHB), poly vinyl alcohol (PVA) poly-hydroxyvalerate (PHV), polyvinylpyrrolidone (PVP), polyethyleneimine (PEI) and lactide/trimethylene carbonate copolymers, chitosan, carboxymethyl chitosan, chitin, pollulan, etc., or blends thereof.

In various embodiments, the protein 105 forming the shell 106 is chosen from human serum albumin, bovine serum albumin, protamine, transferrin, lactoferrin, fibrinogen, gelatin, mucin, soy protein, apoferritin, ferritin, lectin, gluten, whey protein, prolamines such as gliadin, hordein, secalin, zein, avenin, or combinations thereof.

In various embodiments the polymer core 101 is formed by a method that is one of spontaneous emulsification, solvent diffusion, salting out, emulsification-diffusion, micro emulsion, double microemulsion, ultrasonication, nano-precipitation or electrospray. In various embodiments of the method shown in FIG. 1B, the protein shell 106 is formed over the polymer core by simple desolvation, co-acervation, complex co-acervation, nano-precipitation, sol-gel processing, spray drying, salting-out or cross linking and the like. In some embodiments, the prepared core-shell nanomedicine 110 is purified by centrifugation and lyophilisation.

In one embodiment, the core 101 is of average size ≤500 nm and the shell 106 is of average thickness ≤200 nm respectively. In various embodiments, the core and shell are loaded with one or more small molecule kinase inhibitors and chemotherapeutic drugs. In one embodiment, the shell comprises either hydrophilic or hydrophobic therapeutic agents, or both types of agents.

In one embodiment, the small molecule kinase inhibitor is chosen from: the inhibitors of tyrosine kinase including epidermal growth factor receptor inhibitors such as erlotinib, lapatinib, neratinib, gefitinib, mubritinib, afatinib, pelitinib, vandetenib, vascular endothelial growth factor receptor and platelet derived growth factor receptor inhibitors such as brivanib, axitinib, tivozanib, cedivanib, crenalonib, dovitinib, foretinib, linifanib, masitinib, motesanib, pazopanib, ponatinib, regorafenib, fibroblast growth factor receptor inhibitors such as danusertib, PD173074, vargatef, Rous sarcoma oncogene/breakpoint cluster region/Abl inhibitors such as dasatinib, bafetinib, nilotinib, sophoretin, saracatinib, PP121, fingolimod, AT9283, insulin-like growth factor 1 receptor inhibitors such as BMS-536924, BMS-554417, BMS-754807, GSK-1838705A, NVP-ADW742, NVP-AEW541, OSI-906, FLT-3 inhibitors such as cabozantinib, quizartinib, KW 2449, HER-2 inhibitors such as caneratinib, AEE788, BIBW22992, CP-724714, c-Kit such as imatinib, Ki8751, MP-470, OSI-930, telatinib, c-Met such as SUII274, SGX-532, PHA-665752, PF-2341066, PF-04217903, MGCD-265, JNJ-38877605, AMG-208, ALK inhibitors such as LDN-193189, SB-525334, TAE-684, ETA receptor inhibitors such as zibotentan, HIF inhibitors such as 2-methoxyestradiol, Syk inhibitors such as R406, R788, fostamatinib, Tie2 kinase inhibitors such as XL-184, Vascular disrupting agents such as plinabulin, DMXAA, cell cycle/check point inhibitors like polo-like kinase (PLK) inhibitors such as volasertib, BI-2536, BI6727, GSK-461364, HMN-214, ON-01910, cyclin dependent kinase (CDK) inhibitors such as seliciclib, indirubin, flavopiridol, BS-18I, AT-7519, PHA-793887, R547, topoisomerase inhibitors such as adriamycin, camptothecin, etoposide, idarubicin, irinotecan, topotecan, mitoxantrone, microtubule inhibitors such as docetaxel, paclitaxel, vincristine, antimetabolites such as decitabine, gemcitabine, fludarabine, telomerase inhibitors such as BIBR 1532, DNA & RNA replication inhibitors such as clarithromycin, cytarabine, mitoxantrone HCl, dihydrofolate reductase inhibitors such as NSC-131463, methotrexate, HDAC inhibitors such as droxinostat, givinostat, belinostat, vorinostat, panobinostat, mocetinostat, entinostat, valproic acid, Bcl-2 inhibitors such as navitoclax, obatoclax, ABT 737 and TNF-a inhibitors such as lenalidomide, pomalidomide, p53 inhibitors such as JNJ 26854165, NSC 207895, PARP inhibitors such as BSI-201, INO-1001, MK-4827, veliparib, olaparib, MAPK inhibitors such as AS-703026, PD98059, PD0325901, JTP-74057, U0126, GDC-0879, ZM 336372, SP600125, selumatinib, vemurafenib, sorafenib, tipifarnib, PI3K/Akt/mTOR inhibitors such as acadesine, A66, CAL101, BEZ235, GDC-0941, Phenformin, PI-103, quercetin, PP121, XL765, XL147, everolimus, deforolimus, chrysophanic acid, temsirolimus, rapamycin, perifosine, triciribine, integrase and protease inhibitors such as elvitegravir, raltegravir, atazanavir, bortezomib, ritonavir, Wnt/Hedgehog/Notch inhibitors such as cyclopamine, vismodegib, semagacestat, BMS-708163, ICG-001, XAV-939, Jak/STAT inhibitors such as tofacitinib, ruxolitinib, cryptotanshinone, NSC-74859, AZ-960, AG-490, PKC inhibitors such as zoledronic acid, enzastaurin, chelerythrine, TGF-P inhibitors such as LY2157299, SB431542, antioxidant inhibitors such as diethyl-dithiocarbamate, methoxyestradiol, 1-buthionine sulfoximine, 3-amino-1,2,4-triazole or combinations thereof.

In various embodiments, the chemotherapeutic drug is chosen from the group of anti-neoplastic agents such as aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pam idronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine and combinations thereof. In various embodiments, the therapeutic agents 102 and 104 are configured to be delivered by either passive or active targeting. In one embodiment, the active targeting is done by conjugating the core-shell formulation with targeting ligands such as monoclonal antibody against receptors such as, CD20, CD33, CD34, CD38, CD44, CD47, CD52 CD90, CD 123, CD 133, EGFR, PDGFR, VEGF, HER2, transferrin receptors and like, peptides such as R.GD, CRGD, LyP-1, bombesin (BBN), FSH33, truncated human basic fibroblast growth factor (tbFGF), octreotide, small molecules such as folic acid, mannose, hyaluronic acid (HA), proteins such as transferrin, somatostatin or aptamers. In one embodiment, the therapeutic agents are configured to be delivered from the shell and core either sequentially or simultaneously.

Thus, the drug delivery system for delivering combination therapies is achieved as each agent provides the desired maximal effect, independently and without interference. The multi targeted nanoparticle formulation results enhanced anti-cancer activity compared to single drug loaded nanoparticles. Moreover, core-shell construct can be targeted to the diseased site by conjugating with a wide array of cancer targeting ligands and monoclonal antibodies against cancer cell-specific surface antigens includes folic acid, transferrin, and monoclonal antibodies against CD123, CD33, CD47, CLL-1, etc. Such a system would be useful not only in the treatment of cancer but would also find use in the treatment of other diseases such as autoimmune disease (e.g., rheumatoid arthritis), inflammatory diseases (e.g., asthma), neurological diseases (e.g., epilepsy), and ophthalmological diseases (e.g., diabetic retinopathy). Therefore, a core-shell platform developed for sequential and simultaneous delivery of the loaded drugs depending on the nature of the construct such as polymer and protein, its molecular weight, degradation kinetics and nature of drug binding.

The invention is further explained in the following examples, which however, are not to be construed to limit the scope of the invention as defined by the appended claims.

EXAMPLES

Example—1

Figure 2:
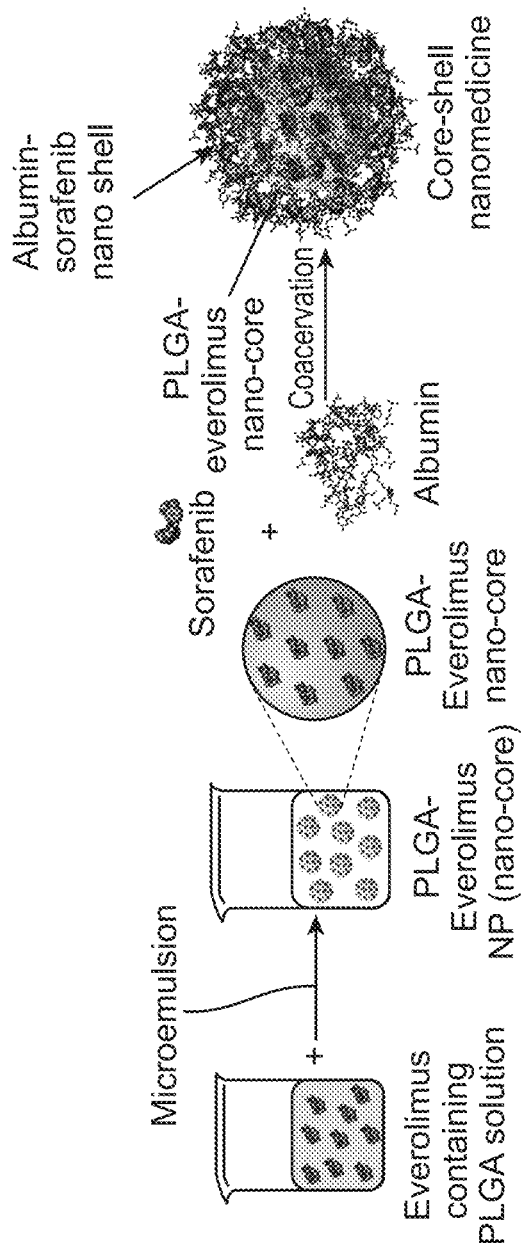
FIG. 2 shows an example reaction scheme including steps involved in the synthesis of the core-shell particle formulation.

In this example, preparation of a combinatorial polymer-protein core-shell particle formulation as shown schematically in FIG. 2 with a mTOR small molecule kinase inhibitor, everolimus loaded polymeric [PLGA: poly(lactic-co-glycolic acid (50:50)] nanocore and a small molecule multi-kinase inhibitor sorafenib entrapped protein shell is presented. 1 mg of everolimus was dissolved in 5 ml 2.5% w/v PLGA-acetone solution and allowed to incubate overnight with continuous stirring at a speed of 500 rpm at 4° C. Emulsification of the polymer-drug solution was achieved by the drop-wise addition of the above solution into 5 ml distilled water containing 0.4% v/v pluronic F-127, with continuous stirring at a speed of 1500 rpm on a magnetic stirrer. Acetone was evaporated out from the o/w emulsion yielding a colloidal dispersion of everolimus loaded PLGA nanoparticles.

The nanoparticles were then recovered from the solution by centrifugation at 5000 rpm for 10 minutes. The harvested nanoparticles were washed with distilled water and the final pellet was resuspended in 5 ml distilled water and lyophilized for 48 h to yield freeze-dried PLGA-everolimus. Albumin-sorafenib was prepared by nano-precipitation wherein briefly, 5 mg of BSA was dissolved in 5 ml of double-distilled water. To this, 64 µL of 15.7 mM DMSO-sorafenib was added drop wise with continuous stirring at a speed of 1500 rpm on a magnetic stirrer. To the resulting colloidal solution, 10 mg of EDC was added and incubated in the dark at 4° C. with continuous stirring (500 rpm). The nano-dispersion of albumin-sorafenib was stored at 4° C. and used as synthesized for further characterization and cell culture studies.

Example—2

In this example, preparation of a combinatorial polymer-polymer core-shell (particle formulation with a chemotherapeutic drug, paclitaxel loaded polycaprolactone (PCL) nanocore and dasatinib encapsulated chitosan shell is presented. 1 mg Paclitaxel was dissolved in 5 ml 1.0 wt % PCL solution in chloroform and allowed to incubate overnight with continuous stirring at a speed of 500 min at 4° C. Emulsification of the polymer-drug solution was achieved by the drop wise addition of the above solution into 5 ml distilled water containing 0.4% v/v pluronic F-127, with continuous stirring at a speed of 1500 rpm on a magnetic stirrer. Chloroform was evaporated out from the o/w emulsion yielding a colloidal dispersion of paclitaxel loaded PCL nanoparticles. The nanoparticles were then recovered from the solution by centrifugation at 5000 rpm for 10 minutes. The harvested nanoparticles were washed with distilled water and the final pellet was resuspended in 5 ml distilled water and lyophilized for 48 h to yield freeze-dried PCL-paclitaxel nanoparticles.

The lyophilized particles are then mixed with 0.5% chitosan solution containing 5 mM sorafenib. 0.25 wt % Tween 80 was added to this solution to prevent particle aggregation and the system was subjected to stirring for 30 min. The chitosan-sorafenib nanoshell was prepared over PCL-paclitaxel nanoparticles by ionic gelation process. Aqueous tripolyphosphate (TPP: 0.25% w/v) solution was added drop wise into the above solution and stirred under room temperature. The core shell nanoparticles were obtained by centrifuging the suspension at 12,000 rpm for 30 min.

Example—3

Figure 3:
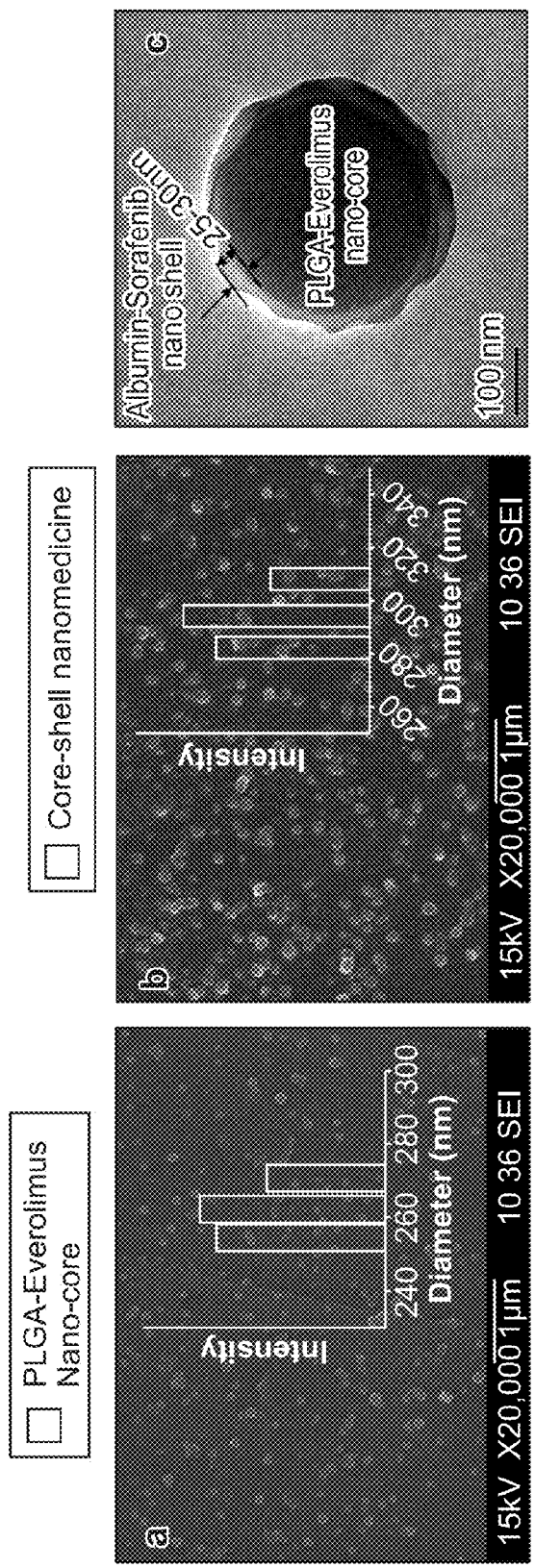
FIG. 3A shows the scanning electron microscopic (SEM) image of the PLGA-Everolimus nano-core.
FIG. 3B shows the SEM image of the final core-shell nanoconstruct.
FIG. 3C shows the SEM image of the PLGA-everolimus core-albumin-sorfenib shell particle formulation.

The size and morphology of the core-shell particle formulation was characterized using dynamic light scattering technique and electron microscopy. In FIG. 3A, the nano-everolimus polymeric core nanoparticle exhibited smooth and regular spherical shape with average size of ~280 nm as observed in scanning electron microscopy (SEM) analysis. The dynamic light scattering measurements also exhibited mean diameter of ~284±20 nm. Zeta potential analysis, revealed an average potential of −15.42 mV, indicative of a good stable dispersion of nano-everolimus in an aqueous medium. Everolimus was efficiently loaded into PLGA nanoparticles attaining an encapsulation efficiency of 94.58±2.56%.

The loading efficiency of sorafenib in albumin shell was ~95%, owing to strong hydrophobic interactions. In FIG. 3B, the SEM images of the final core-shell nanoconstruct indicated an increase in the particle size to ~330 nm, compared to that of nano-core. DLS analysis indicated average particle size of 335 nm±12.6 nm which is in line with SEM analysis which recorded size of the construct to be ~345 nm. The field emission transmission electron microscopic image of a single nano-construct clearly revealed the formation of core-shell structure where electron-dense PLGA-everolimus nano-core was found decorated with a thin (25-30 nm) shell of albumin-sorafenib. Furthermore, the particle formulation suspension exhibited a zeta potential of −10.86 mV. FIG. 3C shows the SEM image of the PLGA-everolimus core-albumin-sorfenib shell particle formulation.

Example—4

Figure 4:
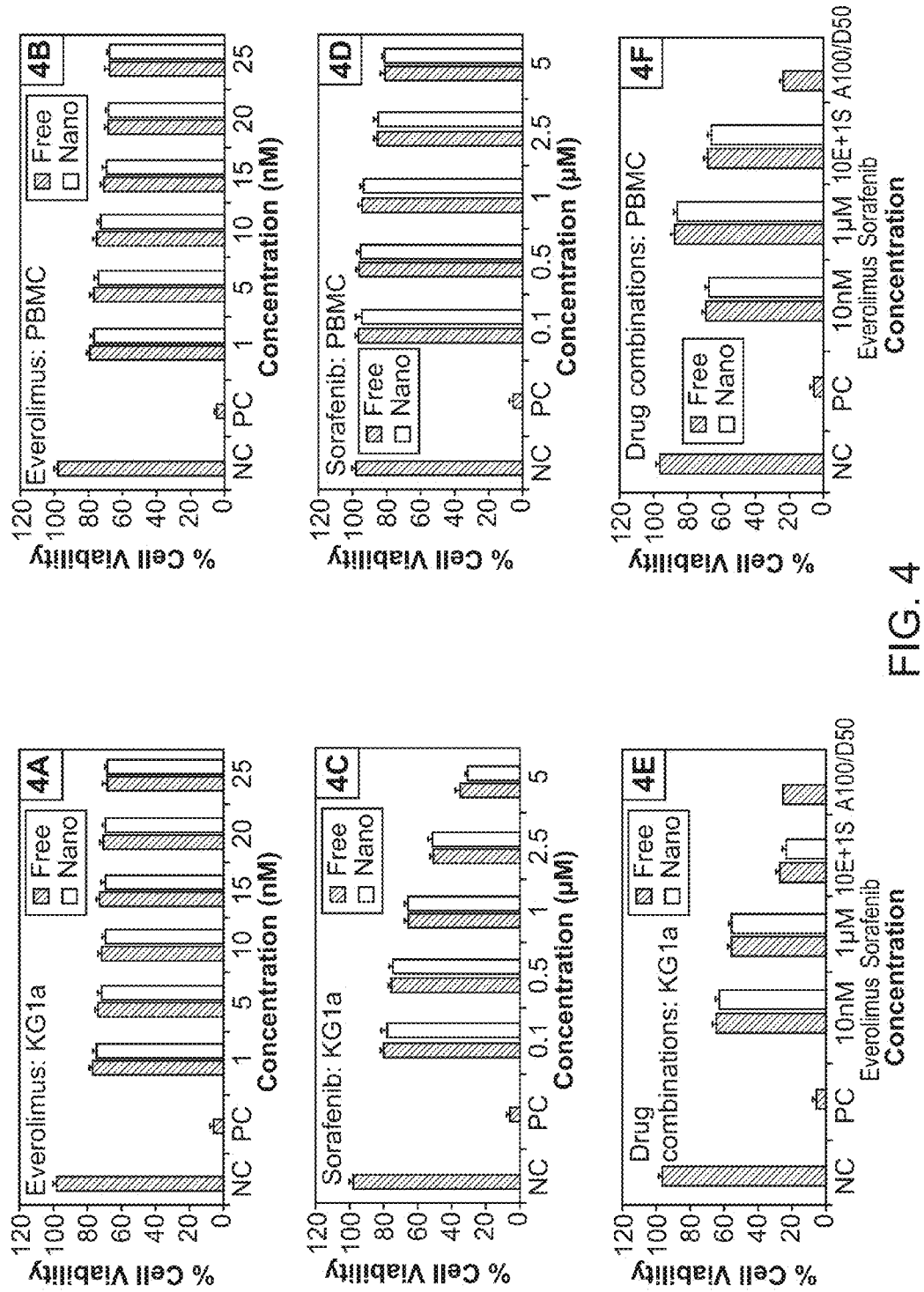
FIG. 4 shows the cytotoxicity of free drugs and nanoformulations of everolimus, sorafenib and combination core-shell particle formulation in KG1a and PBMC. (a1 and a2) Cell viability of free everolimus and nano everolimus (1-25 nM) treated KG1a and PBMC, (b1 and b2) Cell viability of free sorafenib and nano sorafenib (0.1-5 μM) treated KG1a and PBMC (c1 and c2) Cell viability of 10 nM everolimus and 1 μM sorafenib free drug and nanoformulation in KG1a and PBMC in comparison.

In FIG. 4, the cytotoxic potential of the core-shell particle formulation was investigated in Acute Myeloid Leukemia primitive cell line, KG1a, and human peripheral blood derived mononuclear cells, PBMC. To optimize the concentration of the small molecules in core-shell particle formulation, the dose-response of everolimus and sorafenib in KG1a and PBMC was identified. To determine the cytotoxicity of free drugs and nanoformulations, both KG1a and PBMC were treated with respective concentration ranges of everolimus and sorafenib for 72 hours. Both free drugs and nanoformulations of everolimus and sorafenib were shown to exhibit similar toxicity profiles. Free everolimus and nano-everolimus did not exert any significant cytotoxicity towards KG1a, over a concentration range from 1 to 25 nM, which demonstrated its inefficiency as a monotherapy agent in FIG. 4A. However, both free and nano-everolimus showed slight toxicity towards PBMC in FIG. 4B which nevertheless falls within the tolerable limit. This toxicity of everolimus might account from its immunosuppressive properties. In contrast, sorafenib demonstrated concentration dependent toxicity in KG1a, over a concentration range of 0.1 to 5 µM, while causing only minimal toxicity towards PBMC in FIG. 3C, which could be projected as an ideal anti-cancer agent. However, it is clear from FIG. 3D that sorafenib too cannot manifest as an efficient single agent against AML, since ~40% of cells remain viable even after treating them with 5 µM sorafenib for 72 h. Therefore, possible synergistic toxicity by treating cells with a combination of both everolimus and sorafenib are investigated. For this, initially identified the dose-response of currently used cytotoxic drug combination, Ara-C and daunorubicin, replicating the clinically administered concentration ratios under in vitro conditions in KG1a and PBMC. The toxicity level of the 100 nM Ara-C+50 nM daunorubicin was taken as reference for anti-cancer efficacy of nanoformulation, as it ideally represents the clinically administered ratio of both chemotherapeutic drugs. Sub-IC50 concentrations of both everolimus and sorafenib were tested in combination for possible synergism, aiming to further lower the concentration of individual drugs. Therefore in the subsequent set of experiments, KG1a cells were treated with free drug combinations of 10 nM everolimus and 1 µM sorafenib and the core-shell particle formulation encapsulating same concentration of drugs along with the chemodrug combination.

FIG. 4E shows the toxicity exerted by the synergizing combination of drugs. Surprisingly, the cytotoxic profile of the kinase inhibitor combination proved to be as effective as the chemotherapeutic combination. The 10 nM everolimus-1 µM sorafenib free drug combination exerted a toxicity of ~71% compared to A100+D50 chemotherapeutic combination toxicity of ~72%. Whereas, the core-shell particle formulation encapsulating 10 nM everolimus-1 µM sorafenib demonstrated maximal toxicity of the lot, registering ~75% toxicity. Further, from FIG. 4F shows that the 10 nM everolimus-1 µM sorafenib free drug combination and particle formulation exerted minimal toxicity of ~20% towards PBMC, in comparison to lethal toxicity of ~80%, exerted by the chemotherapeutic combination.

The most striking observation from the above results is regarding the excellent synergy exhibited by the combination of sub-IC50 concentrations of everolimus and sorafenib. ~70% of cells treated with 10 nM everolimus and ~68% cells treated with sorafenib remained viable after 72 hours of incubation. Whereas, only 25% cells survived the treatment with the kinase inhibitor combination. In FIGS. 4G and 4H, subsequent experiments using combinations of 25 nM everolimus and 5 µM sorafenib proved to be extremely cytotoxic towards KG1a leaving a 5% surviving population whereas ~74% PBMCs survived the kinase combinatorial treatment, as opposed to ~5% PBMC that survived the corresponding 250 nM Ara-C+125 nM daunorubicin chemotherapeutic treatment.

Example—5

Figure 5:
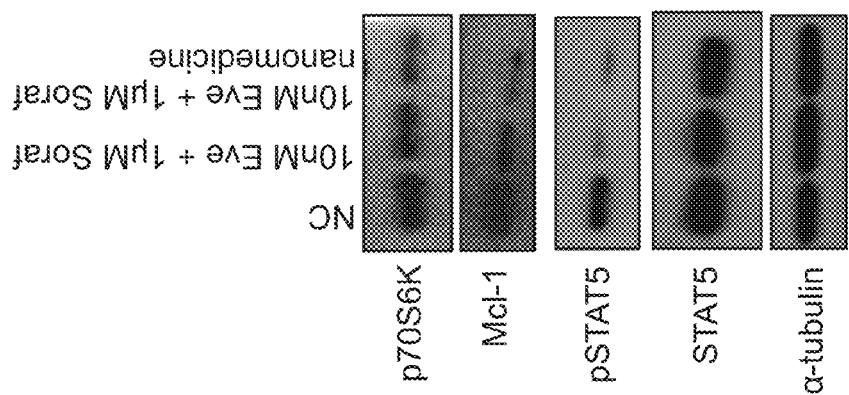
FIG. 5 shows confocal DIC images of (A) untreated KG1a cells (B) 10 nM everolimus and 1 μM sorafenib nanomedicine treated KG1a cells and (C) Western blot analysis of KG1a cells treated with free drug combination and nanomedicine for 72 hours.
Figure 5:
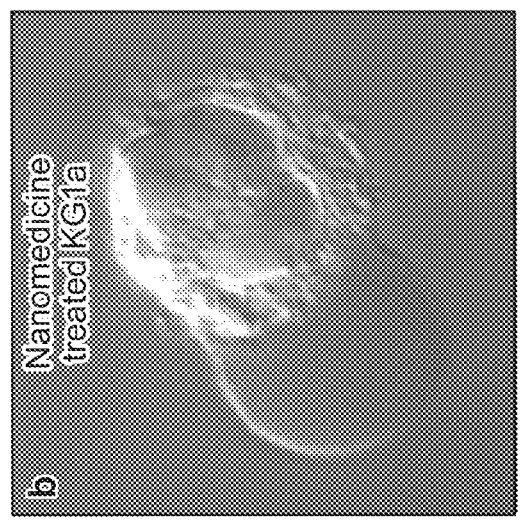
Figure 5:
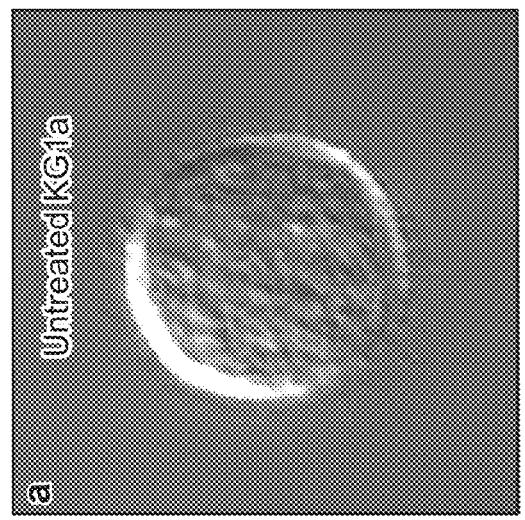

The morphological characterization and western blot analysis of primitive AML cell lines treated with the core-shell particle formulation were analyzed. The particle formulation exerted evident morphological changes and loss of membrane integrity compared to same concentrations of free everolimus and free sorafenib as seen from the confocal DIC image in FIGS. 5A and B. To analyze the extent of mTOR inhibition by everolimus and induction of apoptosis by sorafenib, the phosphorylation status of p70S6 kinase, and Mcl-1 was determined in KG1a treated with the free drug combination and core-shell particle formulation. Both free drug combinations and free drugs were found to attenuate mTOR signaling and reduced the expression level of phospho-p70S6K in FIG. 5C. The observed reduction in phospho-p70S6K was more pronounced in the nano everolimus treated KG1a cells indicating an increasingly efficient delivery of nano everolimus to the cells over the free drug formulation. Similarly, the downregulation of both Mcl-1 and pSTAT5 in both free drug and particle formulation treated KG1a was confirmed through Western blot analysis.

Example—6

Figure 6:
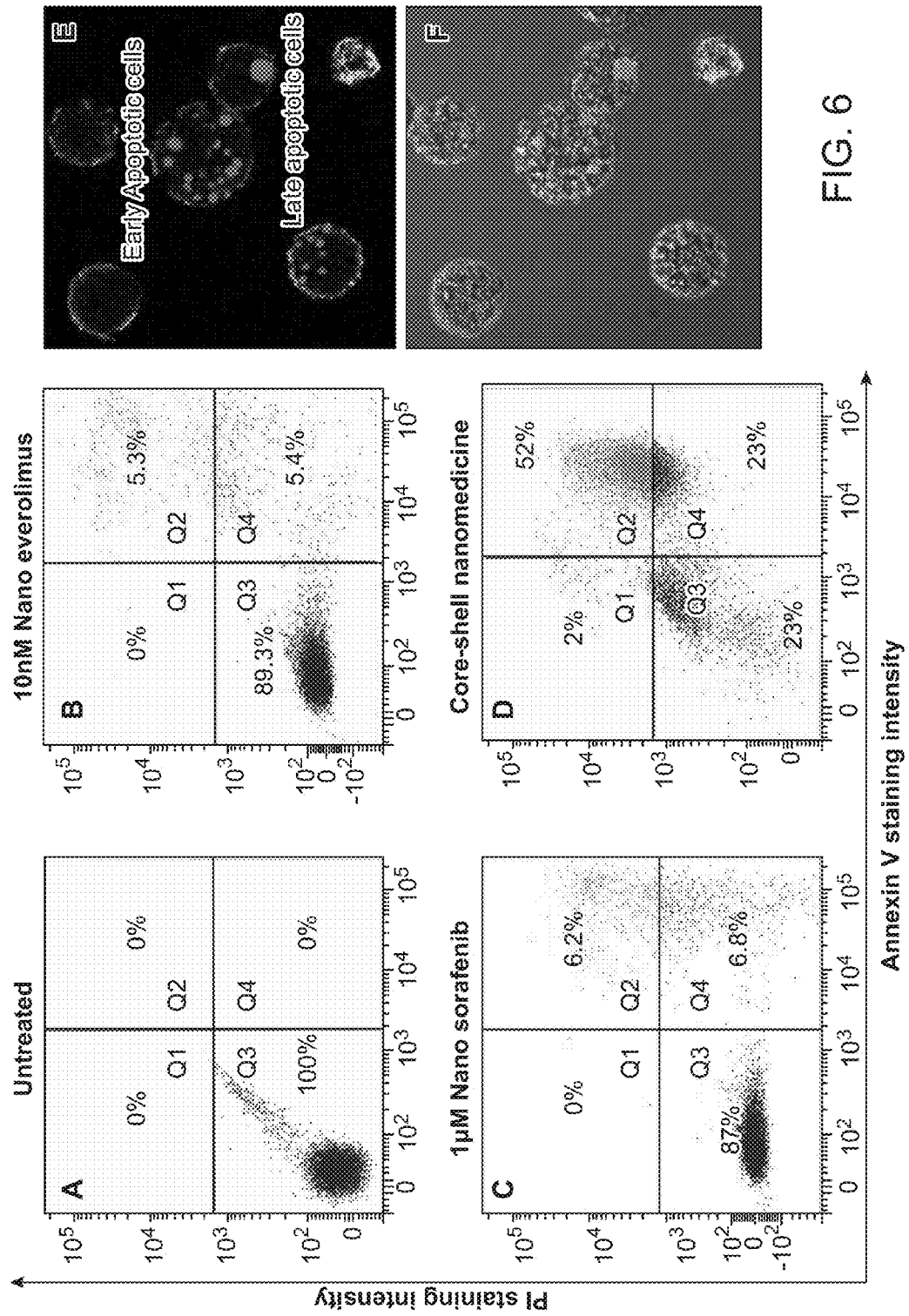
FIG. 6 shows the mode of cell death induced by the particle formulation analyzed using flow cytometry and confocal microscopy.

In another embodiment of the said method, mode of cell death induced by the particle formulation was analyzed using flow cytometry and confocal microscopy in FIG. 6. The cells treated with nano-everolimus, nano-sorafenib and core-shell medicine were stained with FITC conjugated annexin-V and PI and the corresponding flow data and confocal microscopic images shows both apoptotic and late-apoptotic cell fractions in FIGS. 6A, 6B, 6C and 6D.

Primarily, the invention represents a polymer-protein core-shell particle formulation nanoparticle that aids sequential/simultaneous delivery of at least two small molecule kinase inhibitors. Specifically, the core-shell construct is based on a polymeric core made of poly-lactide-co-glycolide co-polymer nanoparticle encapsulating an mTOR inhibitor, everolimus and an albumin nano-shell encapsulating a multi-kinase inhibitor, sorafenib. Moreover, the invention comprises the highly hydrophobic payloads which are incorporated within the polymeric and protein matrix significantly improves therapeutic outcome by enhancing the aqueous solubility, dissolution rate and enhanced uptake by cancer cell specific targeting. The targeting efficacy of the nanoformulation can be achieved by conjugating with a wide array of cancer targeting ligands and monoclonal antibodies against cancer cell-specific surface antigens; the examples of which include folic acid, transferrin, and monoclonal antibodies against CD123, CD33, CD47, CLL-1, etc.

What is claimed is:

1. A core-shell particle formulation for delivering multiple therapeutic agents comprising:
   one or more polymers forming a core, wherein the one or more polymers forming the core comprise poly vinyl alcohol; and
   one or more proteins forming a shell encapsulating the core to form a particle formulation, wherein the one or more proteins forming the shell comprise protamine;
   wherein the core and the shell each comprise one or more therapeutic agents, wherein the one or more therapeutic agents of the core comprise doxorubicin and the one or more therapeutic agents of the shell comprise sorafenib;
   wherein the particle formulation is configured to independently release the therapeutic agents from the core and the shell; and
   wherein the therapeutic agents are configured to be delivered by active targeting, wherein the active targeting is done by conjugating the core-shell formulation with transferrin ligand.

2. The formulation of claim 1, wherein the core is of average size ≤500 nm.

3. The formulation of claim 1, wherein the shell is of average thickness ≤200 nm.

4. The formulation of claim 1, wherein the therapeutic agents of the core and shell further comprise one or more small molecule kinase inhibitors or chemotherapeutic drugs.

5. The formulation of claim 1, wherein the shell comprises one or both of hydrophilic and hydrophobic therapeutic agents.

6. The formulation of claim 1, wherein the one or more polymers forming the core further comprise poly glycolic acid, poly(lactic-co-glycolic acid), glycolide/trimethylene carbonate copolymers, poly-lactides, poly-L lactide, poly-DL-lactide, L-lactide/DL-lactide copolymers, lactide/tetramethyl-glycolide copolymers, poly-caprolactone, poly-valerolacton, poly-hydroxy butyrate, poly-hydroxyvalerate, polyvinylpyrrolidone, or polyethyleneimine and lactide/trimethylene carbonate copolymers.

7. The formulation of claim 1, wherein the one or more proteins forming the shell further comprise human serum albumin, bovine serum albumin, protamine, transferrin, lactoferrin, fibrinogen, or gelatin.

8. The formulation of claim 4, wherein the small molecule kinase inhibitor is chosen from the group consisting of inhibitors of tyrosine kinase, epidermal growth factor receptor inhibitors, vascular endothelial growth factor receptor inhibitors, platelet derived growth factor receptor inhibitors, fibroblast growth factor receptor inhibitors, Rous sarcoma oncogene/Breakpoint cluster region/Abl inhibitors, insulin-like growth factor 1 receptor inhibitors, FLT-3 inhibitors, HER-2 inhibitors, c-Kit inhibitors, c-Met inhibitors, ALK inhibitors, ETA receptor inhibitors, HIF inhibitors, Syk inhibitors, Tie2 kinase inhibitors, vascular disrupting agents, cell cycle/check point inhibitors, polo-like kinase inhibitors, cyclin dependent kinase inhibitors, topoisomerase inhibitors, microtubule inhibitors, antimetabolites, telomerase inhibitors, DNA replication inhibitors, RNA replication inhibitors, dihydrofolate reductase inhibitors, HDAC inhibitors, Bcl-2 inhibitors, TNF-a inhibitors, p53 inhibitors, PARP inhibitors, MAPK inhibitors, PI3K/Akt/mTOR inhibitors, integrase inhibitors, protease inhibitors, Wnt/Hedgehog/Notch inhibitors, Jak/STAT inhibitors, PKC inhibitors, TGF-P inhibitors, antioxidant inhibitors, and combinations thereof.

9. The formulation of claim 4, wherein the chemotherapeutic drug is chosen from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, dasatinib, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine and combinations thereof.

10. The formulation of claim 1, wherein the therapeutic agents are configured to be delivered from the shell and core sequentially.

11. The formulation of claim 1, wherein the therapeutic agents are configured to be delivered from the shell and core simultaneously.

* * * * *